United States Patent [19]

Wason

[11] 4,122,160
[45] Oct. 24, 1978

[54] TOOTHPASTE COMPOSITIONS CONTAINING IMPROVED AMORPHOUS PRECIPITATED SILICAS

[75] Inventor: Satish K. Wason, Havre de Grace, Md.

[73] Assignee: J. M. Huber Corporation, Locust, N.J.

[21] Appl. No.: 729,448

[22] Filed: Oct. 4, 1976

Related U.S. Application Data

[60] Continuation of Ser. No. 519,736, Oct. 31, 1974, which is a division of Ser. No. 286,655, Sep. 6, 1972, Pat. No. 3,893,840.

[51] Int. Cl.$^2$ .................. A61K 7/16; C01B 33/12; C09G 1/02; C09K 3/14
[52] U.S. Cl. ........................... 424/49; 51/308; 106/288 B; 252/317; 423/335; 423/339; 424/357
[58] Field of Search .................. 424/49, 357; 423/335, 423/339; 106/288 B; 252/317; 51/308

[56] References Cited

U.S. PATENT DOCUMENTS

| | | | |
|---|---|---|---|
| 2,731,326 | 1/1956 | Alexander et al. | 23/182 |
| 2,994,642 | 8/1961 | Bossard | 424/49 |
| 3,004,921 | 10/1961 | Stossel | 252/309 |
| 3,235,331 | 2/1966 | Nauroth et al. | 23/182 |
| 3,538,230 | 11/1970 | Pader et al. | 424/50 |
| 3,689,637 | 9/1972 | Pader | 424/52 |
| 3,705,940 | 12/1972 | Kirchgassner | 424/49 |
| 3,864,470 | 2/1975 | Watson | 424/49 |
| 3,939,262 | 2/1976 | Kim | 424/52 |
| 4,007,260 | 2/1977 | Kim | 424/52 |

FOREIGN PATENT DOCUMENTS

| | | | |
|---|---|---|---|
| 2,206,285 | 8/1973 | Fed. Rep. of Germany | 424/49 |
| 2,154,376 | 5/1973 | Fed. Rep. of Germany | 424/49 |
| 49-080,256 | 8/1974 | Japan. | |
| 7,304,942 | 1/1974 | South Africa. | |

OTHER PUBLICATIONS

Chem. Abstracts, vol. 79 #23514r of Ger. 2,154,376 of Kirchgassner.
Chem. Abstracts, vol. 79 #149296g of Ger. 2,206,285 of Kirchgassner.
Gershon et al. "References" Chap. 14, pp. 423-531 of vol. 1, (1972) Cosmetics, Science & Technology, Balsam et al. Wiley-Interscience, N.Y. N.Y.

*Primary Examiner*—Shep K. Rose
*Attorney, Agent, or Firm*—Harold H. Flanders

[57] ABSTRACT

A method for producing precipitated silicic acid products and silicates having a unique combination of physical and chemical properties is disclosed. The products are produced by acidulating a solution of an akali metal silicate with an acid until precipitation just begins. At this point the reaction mass is aged for a period of time and thereafter the acid addition is continued until the precipitated product is obtained. Products produced in accordance with the invention exhibit lower wet cake moisture (or higher percent solids) and are characterized by their low structure, low oil absorption, high abrasiveness and high pack density. The products can be used as abrasive and polishing agents in dentifrice compositions, in the production of molecular sieves, in paints and the like. In a particularly advantageous embodiment, an adduct material, such as aluminum, is added to control the refractive index of the precipitated silica. Products produced in this manner have particular utility for use as abrasion and gelling agents in clear toothpaste compositions.

2 Claims, No Drawings

TOOTHPASTE COMPOSITIONS CONTAINING IMPROVED AMORPHOUS PRECIPITATED SILICAS

This is a continuation of application Ser. No. 519,736, filed Oct. 31, 1974, abandoned, which is the divisional of Ser. No. 286,655, filed Sept. 6, 1972, now U.S. Pat. No. 3,893,840.

BACKGROUND OF THE INVENTION

1. Field of the Invention

The present invention relates to the production of precipitated silicas and, more particularly, to a novel process for producing synthetic precipitated silicas and silicates having new and improved physical and chemical properties.

2. Description of the Prior Art

As known in the art, finely divided amorphous precipitated silicic acid products and certain zeolitic type alumino silicates may be prepared by the acidulation of an aqueous silicate solution with an acid or a salt of the acid, such as aluminum sulfate. Such products are commercially available being sold e.g., under the trademarks "Zeo"; "Zeolex" and "Arogen" by the J. M. Huber Corporation. Specific examples of these products as well as methods for their preparation are disclosed in U.S. Pat. Nos. 2,739,073; 2,843,346 and 3,582,379.

While the nature or characteristics of the above discussed precipitated silicic acid (sometimes herein referred to as silicas) and silicates depend, in part, on the chemistry of the silicate solution (specifically the $SiO_2$/$Na_2O$ ratio of the silicate) as well as the reaction conditions employed (precipitating pH, etc.), prior to the present invention such silicas were characterized by the following properties: high structure, high wet cake moisture content, high oil absorption, low valley abrasion, high surface area and low pack density. In this regard, and due in part to the properties such as high oil absorption, high surface area, etc., the silicas have been widely and successfully used as reinforcing materials in rubber, in paints, in the manufacture of paper, as moisture conditioners and the like.

However, the generally speaking for the moment, the high wet cake moisture content is disadvantageous in that the drying and filtration rates are decreased thus increasing the overall cost in the production of the final product. For example, in the conventional production of silicic acid materials as defined above the wet cake moisture content of the product (following filtration of the precipitated reaction mass) is approximately 82%. This means that there can be recovered only 18 parts of dry silica from 100 parts of wet cake.

Further, and very importantly, the low abrasiveness and high refractive index of known silica and silicates renders them unsuitable for many uses. For example, it is well known that conventional synthetic precipitated silicas are unsuitable as polishing and abrasive agents in toothpaste compositions. See German Pat. No. 974,958; French Pat. No. 1,130,627; British Pat. No. 995,351; Swiss Pat. No. 280,671 and U.S. Pat. 3,250,680. In this regard, it is disclosed in U.S. Pat. No. 3,538,230 that known amorphous silicas such as precipitated silicas, pyrogenic silicas and aerogels are unsuitable for dentifrice use because they show substantially no cleaning ability on human teeth because of their initial small particle size and because of the ease in which they break down into small particle sizes which result in poor cleaning ability.

Further, and in more detail, conventional silicas and amorphous precipitated alumino silicates, such as "Zeolex" and "Arogen", cannot be used for a clear gel toothpaste because of their high refractive index (1.55) and because they lack the needed abrasive and polishing characteristics when added to the toothpaste base composition. Clear gel toothpaste contains a high percentage of abrasive and polishing agent in the toothpaste formula. The major function of the abrasive and polishing agent is to remove stains, food debris and bacterial plaque from the human tooth surface. Ideally the polishing agent should provide a maximum cleaning action at acceptable abrasion levels and must be compatible at high loadings of 15% up to 50% with other toothpaste formula ingredients. Thus known silicas and alumino silicates are unsuitable for clear gel toothpastes, (such as the product sold under the Trademark "Close-up" by Lever Brothers) because they cannot be added at high loadings of 15% and above in a typical toothpaste composition. Because of their high oil absorption, high sorption characteristics and high refractive index (1.55) known precipitated pigments thicken up the dentifrice composition and impart undesirable opacity to the base paste resulting in an unacceptable product. In summary of the above, precipitated silicas and silicates cannot be used in conventional and clear gel dentifrice compositions because such products result in unacceptable toothpaste consistencies and do not possess the acceptable abrasive and polishing characteristics needed for use in dentifrice compositions.

SUMMARY OF THE INVENTION

In summary, the present invention relates to the production of synthetic precipitated silicas and silicates having new and improved physical and chemical characteristics. More particularly, the invention is directed to a new and unique process for producing precipitated silicas and silicates having low structure, low wet cake moisture content, high abrasion, low surface area, low oil absorption and high pack densities. Because of such properties the improved silicas can be advantageously and effectively used as an abrasive and polishing agent in dentifrice compositions. In addition the new products can be advantageously employed in further applications such as in the preparation of molecular sieves, as flatting and texturizing agents, as fillers and carriers and as viscosity control agents.

Stated broadly, the method of the invention embodies the concept and is based on the discovery that if the addition of the acid to the silicate solution is interrupted at the first appearance of the opalescence point (i.e., that point at which precipitation first begins) the resulting silicas possess the aforementioned unique combination of properties. Stated differently, the low structure silicas of the invention are prepared by acidulating the aqueous alkali metal silicate solution (i.e., sodium silicate) until precipitation just begins. At this point the reaction mass is aged for a suitable length of time generally on the order of from about 15 to 20 minutes. After the aging period, the introduction of the acid is continued until the precipitated product is obtained. In accordance with a further method embodiment it has been found that the properties of the silicas can be closely and accurately controlled if the acid and a portion of the alkali metal silicate are added simultaneously so that the reaction is carried out at an essentially constant pH.

In accordance with a third and particularly advantageous method embodiment, the acidulating agent, such as sulfuric acid, is pre-mixed with an adduct such as aluminum (which is preferably added as a water soluble salt thereof, as for example, aluminum sulfate). In this regard it has been found that the addition of the adduct, coupled with the aging of the reaction mass, substantially controls the refractive index of the resulting silica while at the same time not effecting the significant increase in the abrasiveness.

As briefly noted above, the precipitated silicas produced in accordance with the invention results in materials of lower processing costs, better packaging characteristics and a unique balance of physical/chemical properties as compared to conventionally precipitated silicas.

It is accordingly a general object of the present invention to provide a novel process for producing precipitated silicas having improved physical and chemical properties.

Another and more particular object is to provide a unique process for producing synthetic amorphous precipitated siliceous products which have particular utility for use as abrasive and polishing agents in dentifrice compositions.

Yet another object is to provide a highly efficient and improved process for producing silicic acid product which exhibits lower wet cake moisture or higher percent solids and which have high valley abrasion and low oil absorption characteristics.

Yet still another object is to provide novel synthetic amorphous precipitated siliceous pigments which are useful as abrasion and gelling agents in clear toothpaste compositions.

A further object is to provide a new process for producing precipitated amorphous silicas which have a unique balance of physical and chemical properties as compared to conventionally known precipitated silicas, said process further resulting in lower processing cost.

A still further object is to provide a process for producing low structure, low wet cake moisture, low surface area, low oil absorption, high valley abrasion and high pack density precipitated silicic acid products.

DESCRIPTION OF PREFERRED EMBODIMENTS

As briefly discussed above, when an acid is added to a solution of an alkali metal silicate, the resulting reaction medium remains clear until such point that a slight turbidity (called the opalescence point) appears. As the acid addition is continued, the silicic acid or silica starts precipitating until all of the silicate solution is precipitated. In conventionally known processes, the pH of the reaction mass is then adjusted to a range of from about 5.5 to 6.5 and the mass is filtered, washed and dried.

In accordance with the present invention, it has been discovered that if the acid addition is interrupted for a suitable period of time at the first appearance of opalescence, the resulting silica possesses a unique combination of physical and chemical properties as well as improved processing advantages. More specifically and again as briefly noted above, the new silicic acid products produced in accordance with the invention exhibit lower wet cake moisture (or higher percent solids) thereby permitting increased drying filtration rates. Further the new silicas have been found to have low structure, relatively low surface areas, low oil absorption, high pack densities and high valley abrasion. Because of these properties, the new silicas are particularly suitable and adapted for use as an abrasive and polishing agent in toothpaste compositions. Other properties include controlled particle size, better dispersion and improved wetting and viscosity characteristics.

At this point it may be noted that as used herein the term "structure" is intended to include, and is defined as, the ability of a silica or silicate material to hold water in its wet cake. When silicas or silicates such as the aforementioned conventional precipitated silicas, hold a high percentage of water i.e, in the neighborhood of 70% to 85%, they are known and referred to as high structure silicas. Materials holding less than 70% and preferably in the neighborhood of from about 50% to 70% water in their wet cake are referred to as low structure silicas.

Turning now to more specific details, in the practice of the invention a solution of the alkali metal silicate is first charged to a reactor and the solution is heated to a temperature in the range of from about 100° F. to 200° F., preferably on the order of from about 150° F. to 175° F. In general and except as otherwise expressly noted herein, the reaction temperatures and rates as well as the concentration of the reactants, i.e., the silicate solution and acid, are the same as in the above discussed known processes for producing precipitated silicic acid products. However, in the practice of the invention it has been found that particularly advantageous results are obtained if the concentration of the silicate solution is on the order of from about 1.0 to about 2.5 pounds/gallon. The acidulating agent or acid, e.g., sulfuric acid, is next charged to the reactor until the slight turbidity (i.e., the opalescent point) first occurs. At this time the acid addition is stopped and the reaction is aged for a period of time on the order of from about 10 minutes to 1 hour. As to be discussed in more detail hereinafter, while the point or time at which the acidulation is discontinued is critical, it has been found that the aging period is generally dictated by process economics. For example, although the reaction mass must be aged for at least 10 minutes to obtain the aforementioned unique combination of properties, it has been found that aging for a period of longer than 2 hours does not, in fact, produce any particular advantage. Therefore from an economic standpoint, the aging period is preferably on the order of from about 10 to 15 minutes.

In accordance with one method embodiment of the invention, it has been found that a more homogeneous product can be obtained when from about one-half to two-thirds of the total silicate is initially charged to the reactor, and the remaining silicate is added simultaneously with the acid in a manner such that the reaction is carried out at a substantially constant pH, preferably on the order of from about 8.5 to 10.5. After the silica has been precipitated, the pH of the resulting slurry is reduced to from about 5.5 to 7.0 by the addition of an excess of the acid.

In a further method embodiment, it has been found that the refractive index of the precipitated silica can be controlled by the addition of an adduct element (such as aluminum, magnesium and the like) to provide an abrasive or polishing agent for a clear translucent or transpartent toothpaste composition. Thus in this embodiment, the acid is premixed with a solution of the adduct material i.e., aluminum (preferably in the form of a water soluble salt such as aluminum sulfate, etc.) and the acid-metal salt mixture is then used for acidulating the aqueous alkali metal silicate until the precipitation just begins. At this point, and similarly as in the other embodiments, the acid and metal salt addition is interrupted and the reaction slurry is aged. After the aging, the addition of the acid-metal salt mixture is continued until the precipitated of the product is complete.

As will be seen from the above the starting materials or reactants employed in the present invention include alkali metal silicates, an acid and a water soluble metal salt. As used herein, the term alkali metal silicates include all the common forms of alkali silicates as, for example, metasilicates, disilicates and water glass. Water soluble potassium silicates and sodium silicates are particularly advantageous. Because of their relatively low cost, sodium silicates are preferred. If employed, sodium silicates are effective in any composition in which the mole ratio of the $SiO_2$ to $Na_2O$ is from about 1 to 4. In this regard commercially available sodium silicate solutions are more or less polymerized depending on their silica to sodium oxide ($SiO_2/Na_2O$) ratios. For example, sodium meta - silicate solution (mole ratio unity) is known to be predominantly monomeric in character while water glass (mole ratio 3.3) is both monomeric and polymeric in character. As the silica to sodium oxide mole ratio of sodium silicate increases, so does the polymer to monomer ratio of its silicate anions. While sodium silicates having an $SiO_2/Na_2O$ mole ratio of from 1 to 4 may be employed, it has been found that particularly advantageous results are obtained if the $SiO_2/Na_2O$ ratio is in the range of from about 2.0 to 2.7.

While the acidulating agent or acid is preferably a strong mineral acid, such as sulfuric acid, nitric acid and hydrochloric acid, it should be understood that other acids, including organic acids, as for example, acetic acid, formic, or carbonic acid can be employed. The adduct material, employed to control the refractive index of the precipitated product may comprise metals such as aluminum, magnesium, zinc and calcium. However, the adduct is preferably employed in the form of a water-soluble salt of the metal which should be compatible with the acid used for precipitation. For example, aluminum salts useful in the method of the invention are the water soluble salts of aluminum and strong acids such as aluminum sulfate, aluminum chloride, aluminum nitrate, and ammonium alum. The amount of the adduct or metal employed may vary depending upon the particular refractive index required. As shown in the following examples an excess of the adduct (e.g., $Al_2(SO_4)_3$) will increase the refractive index to a level above that required for clear dentifrice compositions (i.e., 1.475). However refractive indices above 1.475 may be particularly suitable for many applications and the gist of this method embodiment lies in the discovery that the use of the adduct serves to control this property. The acidulating agent or acid is preferably added as a dilute solution thereof. Preferred results are obtained if the acidic solution is from about 10 to 25% by weight acid based on the total weight of the solution. However this may vary depending upon the particular acid employed, etc. The invention will be further illustrated by the following examples.

EXAMPLE 1

30 gallons of a 1.24 lbs/gal. sodium silicate solution ($SiO_2$ to $Na_2O$ molar ratio of 2.5) was added to the stirred reactor and the silicate solution was heated to 185° F. Sulfuric acid of 11.2% concentration was added to the reactor at the rate of 0.81 gallons per minute till a pH of 10.0 plus or minus 0.1 was reached. At this pH, the precipitation of silica micelles just started. The acid was shut off and the reaction medium was aged for ten minutes. After the aging period, both acid and silicate were added simultaneously at the rate of 0.84 and 1.0 gallons per minute respectively. The silicate was turned off after thirty minutes, the acid addition was continued and the batch was finished off at pH 5.8, filtered washed, dried and milled. The results of this and further examples are shown and summarized hereinbelow.

EXAMPLE 2

In this experiment, 35 gallons of 1.24 lbs/gal. silicate of $SiO_2$ to $Na_2O$ molar ratio of 2.5 were added to the stirred reactor and the silicate solution was heated to 175° F. Sulfuric acid of 11.4% concentration was added to the reactor at the rate of 0.84 gallons per minute till a pH of 10.1 plus or minus 0.1 was reached. At this pH, the precipitation of silica micelles just started. The acid was shut off and the reaction medium was aged for fifteen minutes. The aging step is important to obtain homogeneous product and for the silica micelles to reach an equilibrium condition. After the aging period, both acid and silicate were added simultaneously at the rate of 0.84 and 1.4 gallons per minute respectively. Silicate was turned off after twenty-five minutes; acid addition was continued and the batch was finished off at pH 5.5, filtered, washed, dried and milled. In further tests it was found that a range of products can be made by introducing more than one aging step during the process and by maintaining the precipitation pH substantially constant and within the range of pH 7–10.

EXAMPLE 3

In this experiment, ten gallons of 1.24 lbs/gal. sodium silicate of $SiO_2$ to $Na_2O$ molar ratio of 2.5 were added to a stirred reactor and the solution heated to 175° F. Sulfuric acid of 11.4% concentration was added to the reactor at the rate of 0.12 gallons per minute until the silica just started precipitating. At that time the reaction pH was 10.1. The acid addition was stopped and the reaction medium was aged for fifteen minutes. After the aging period, the acid addition was resumed again until the reaction pH of 9.0 was acheived. At this point the acid was stopped again for 15 minutes and the reaction medium was aged. After aging period was over, silicate was only added to the reactor at the rate of 0.1 gallons per minute until pH of 10.0 was reached. Acid addition was resumed again and the batch was finished off at pH 5.7. The idea of aging at pH 9.0 was to have the silica particles grow to a bigger size and to obtain a final product with lower structure, lower surface area and higher pack density than the conventional silica.

EXAMPLE 4

In this example, five gallons of 1.24 lbs/gal. sodium silicate of $SiO_2$ to $Na_2O$ molar ratio of 2.5 were added to the stirred reactor and the silicate was heated to 175° F. Acid of 10.5% concentration was added to the silicate till a turbidity or faint precipitation appeared in the reactor. Acid was stopped at this point and the reaction medium was aged for twenty minutes. After the aging period, five gallons of silicate and 11.4% acid were added simultaneously at the rate of 0.20 to 0.12 gallons per minute and the batch was finished off at pH 5.5, filtered, washed, dried and milled.

EXAMPLE 5

The procedure of Example 4 was repeated except that six gallons of silicate were added to the reactor and the remaining four gallons were added after the aging period along with the acid.

cate with 11.4% acid till the final pH of 5.5 was obtained. In the control batch no aging step was involved so that the properties of material produced via the new process could be compared with the control batch.

Data on precipitated silicas obtained in Examples 1 thru 10 are summarized below:

| Example | Description | % Wet Cake Moisture | Surface Area (m²/g) | Oil Absorption cc/100g | Density Pour, Pack (lbs/cu.ft) | | Valley Abrasion mg loss |
| --- | --- | --- | --- | --- | --- | --- | --- |
| 1 | Silica via aging | 65 | 66 | 85 | 11.2 | 18.7 | 15.0 |
| 2 | Silica via aging | 55 | 38 | 81 | 14.2 | 27.7 | 17.3 |
| 3 | Silica via aging | 70 | 66 | — | 9.9 | 19.5 | 6.7 |
| 4 | Silica via aging | 53 | 29 | 66 | 18.4 | 33.7 | 83.5 |
| 5 | Silica via aging | 59 | 116 | 108 | 14.2 | 26.0 | 15.3 |
| 6 | Silica via aging | 59 | 46 | 108 | 13.9 | 26.0 | 16.3 |
| 7 | Silica via aging | 62 | 80 | 83 | 12.5 | 22.2 | 18.8 |
| 8 | Silica via aging | 60 | 242 | 95 | 12.7 | 23.9 | 28.4 |
| 9 | Silica via aging | 56 | 38 | 81 | 17.8 | 29.7 | 18.6 |
| 10 | Control (no aging) | 82 | 150 | 211 | 6.3 | 10.7 | 2.5 |

EXAMPLE 6

The procedure of Example 4 was repeated except that seven gallons of silicate were added to the reactor and the remaining three gallons were added simultaneously with acid after aging the reaction medium. The batch was processed similar to Example 4.

EXAMPLE 7

The procedure of Example 2 was repeated except that after the aging period, the precipitation pH was controlled at pH 9.9 plus or minus 0.1. The batch was finished and processed similar to Example 2.

EXAMPLE 8

The procedure of Example 4 was repeated except that the finishing pH was brought down to 3.2. Lower finishing pH results in product of higher surface area.

EXAMPLE 9

In this Example 7½ gallons of 1.24 lbs/gal. sodium silicate were added to the stirred reactor and heated to 175° F. Acid of 11.4% concentration was added till the precipitation of silica particles just began. Acid was then stopped and the reaction medium was aged for fifteen minutes. After the aging period, 7½ gallons of silicate and 11.4% acid were added simultaneously at the rate of 0.3 GPM and 0.18 GPM (gallons per minute) respectively and the batch was finished off at pH 5.6 and the batch was processed similar to Example 4 above.

EXAMPLE 10

A control batch of conventional precipitated silica was prepared by neutralizing 1.24 lbs/gal. sodium sili- From the above data, it is clear that the new process of the invention results in silicas of lower wet cake moisture, lower structure, lower oil absorption, lower surface area, higher pack density and higher valley abrasion than conventional precipitated silicas.

The new process leads to silicas of lower processing costs than regular precipitated silicas. For example, the average wet cake moisture of silicas via the new process is only 60% as opposed to 82% for regular silica (see control). This means I can recover 40 parts of dry silica from 100 parts of wet cake if the silica is produced via the new process. Regular processes result in recovery of about 18 parts of dry silica per 100 parts of wet cake. Thus, via the new process I can recover 22 parts or more of dry silica or an increase of (22/18) × 100 or 122%. The new process results in silicas of better drying and filtration rates and hence significantly lower processing costs than the precipitated silicas produced by the conventional process.

EXAMPLE 11

In a series of tests the general procedures of Examples 1–10 were repeated except that the precipitating pH and the period of aging were varied. The pH was varied in the range of from about 5.5 to 11.0. The aging period was varied from about 5 minutes to 1 hour. The results of these tests were substantially the same as that of Examples 1–10 except that it was found that products of predetermined properties and characteristics (i.e., a specific structure or wet cake moisture content) could be obtained by varying the above process conditions within the specified ranges. These tests also established that if the final batch pH was reduced to below about 5.0 an increase in the surface area was obtained. Thus if it is desired that the final product have a low surface area then the pH of the final batch should be maintained above 5.0. Also these tests established that aging for periods of less than about 8–10 minutes was generally ineffective to produce the low structures, etc. products of the invention.

EXAMPLE 12

The general procedure of Examples 1–11 were repeated except that nitric acid, hydrochloric acid, acetic acid and formic acid were substituted for the sulfuric acid. The results were substantially the same as in Examples 1–11.

EXAMPLE 13

In a series of tests the general procedures of Examples 1–12 were repeated except that aqueous sodium silicates having mol ratios ($SiO_2/Na_2O$) in the range of from 1 to 4 were substituted for the 2.5 silicate of Examples 1–12. The results were substantially the same as above except that it was found that the wet cake moisture content was lower when the 2.5 silicate was employed. In addition the surface area was found to be substantially lower when 2.5 mol ratio silicate was employed. In this regard, in a series of tests the wet cake moisture content and the surface area were compared for silicic acid products produced by prior known techniques (non-aged) and products produced in accordance with the present invention. The results are shown in FIGS. 1 and 2.

The following Examples serve to illustrate the third method embodiment of the invention, i.e., the addition of the adduct material to control the refractive index.

EXAMPLE 14

In this experiment 100 parts by volume of 11.4% sulfuric acid was pre-mixed with 3 parts of 1.38 lbs/gal. aluminum sulfate. This acid-aluminum sulfate mixture was used to precipitate the alumino silicate of controlled refractive index. Thirty-five (35) gallons of 1.24 lbs/gal. silicate of $SiO_2$ to $Na_2O$ molar ratio of 2.6 were added to the stirred reactor and the silicate solution was heated to 175° F. Mixed acid-aluminum sulfate solution was added to the reactor at the rate of 0.84 gallons per minute until reaction pH of 10.1 plus or minus 0.1 was reached. At this pH, the precipitation of aluminum silicate micelles just started. The acid-aluminum sulfate addition was discontinued and the reaction medium was aged for fifteen minutes. The aging or digestion step was found to be important to obtain a homogeneous product and for the alumino silicate micelles to reach an equilibrium condition. After the aging period, both acid-aluminum and silicate solutions were added simultaneously at the rate of 0.84 and 1.4 gallons per minute, respectively. Silicate addition was turned off after twenty-five minutes; mixed acid-aluminum sulfate addition was continued and the batch was finished off at pH 5.5, filtered, washed, dried and milled in the conventional manner. In a series of tests it was found that a range of products could be made by introducing more than one aging step during the process and by maintaining the precipitation pH substantially constant and within the range of about 7–10.

EXAMPLE 15

A control experiment was performed by using the precipitation procedure of Example 14, but by using no aging step.

EXAMPLE 16

The procedure of Example 14 was repeated except the acid/aluminum sulfate ratio was varied by mixing 100 parts of 11.4% sulfuric acid with 11.4 parts of 1.38 pounds per gallon aluminum sulfate.

EXAMPLE 17

A control experiment was performed as per the procedure of Example 16, but without using the aging step.

EXAMPLE 18

Example 14 was repeated by using acid-aluminum sulfate mixture of 100 parts of acid to five parts of aluminum sulfate.

EXAMPLE 19

A control experiment was performed as per the procedure of Example 18 but without using the aging step.

EXAMPLE 20

The procedure of Example 14 was repeated except that the acid and aluminum sulfate were pre-mixed in the ratio of 100:7.0.

EXAMPLE 21

The procedure of Example 14 was repeated but only acid was added up to the aging step. After the aging period, acid, silicate and aluminum sulfate were added simultaneously to the reactor. Both the silicate and aluminum sulfate additions were discontinued after twenty-five minutes. Acid addition was continued until final pH of 5.5 was obtained. The batch was processed similar to Example 13.

EXAMPLE 22

The procedure of Example 21 was repeated except that sodium silicate contained 3% sodium sulfate. The effect of sodium sulfate was that the final product was more abrasive than the one produced in Example 20.

EXAMPLE 23

The procedure of Example 14 was repeated except that acid-aluminum sulfate were pre-mixed in the ratio 100 to 2.5.

The following Table summarizes the data obtained in Examples 14–23. From the following it will be seen that silicate products of controlled refractive index and abrasiveness can be tailored by way of the process of this invention.

TABLE 1

| Example | Description | % $Al_2O_3$ | % WCM | ($m^2/g$) Surface Area | Oil Abs. (cc/100g) | Valley Abrasion | Refractive Index |
|---|---|---|---|---|---|---|---|
| 14 | SAS* via aging | 0.69 | 60 | 106 | 90 | 15.0 | 1.450 |
| 15 | Control-no aging | 0.69 | 79 | 161 | 203 | 2.7 | 1.446 |
| 16 | SAS via aging | 2.12 | 58 | 295 | 99 | 15.9 | 1.464 |
| 17 | Control-no aging | 2.12 | 76 | 250 | 203 | 3.6 | 1.464 |
| 18 | SAS via aging | 0.90 | 56 | 198 | 85 | 17.1 | 1.451 |

TABLE 1-continued

| Example | Description | % $Al_2O_3$ | % WCM | ($m^2/g$) Surface Area | Oil Abs. (cc/100g) | Valley Abrasion | Refractive Index |
|---|---|---|---|---|---|---|---|
| 19 | Control-no aging | 0.90 | 79 | 232 | 219 | 2.3 | 1.451 |
| 20 | SAS via aging | 1.20 | 58 | 246 | 90 | 5.3 | 1.454 |
| 21 | SAS via aging | 0.70 | 58 | 202 | 99 | 9.0 | 1.448 |
| 22 | SAS via aging | 0.73 | 55 | 111 | 80 | 59.5 | 1.437 |
| 23 | SAS via aging | — | 56 | 87 | 74 | 11.5 | 1.450 |

*SAS is Sodium Alumino Silicate.

From the above data, it will be seen that the new process results in alumino silicates of lower structure, lower wet cake moisture, lower oil absorption and higher valley abrasion than the conventional precipitated alumino silicates. Note that the controls of Examples 15, 17 and 19 exhibit high oil absorption and low valley abrasions and hence cannot be used for clear gel toothpaste because they provide unacceptable abrasion characteristics and thicken up the toothpaste base even at low loadings of up to only 8%. In general, refractive indices of from about 1.445 to 1.475 are needed and required for clear gel cosmetic dentifrice use.

EXAMPLE 24

In a series of tests the general procedures of Examples 14–23 were repeated except that nitric acid, hydrochloric acid, acetic acid and formic acid were substituted for the sulfuric acid. The results were substantially the same as in Examples 14–24.

EXAMPLE 25

In a series of further tests the procedures of Examples 14–24 were repeated except that the precipitation pH, the period of aging as well as the $SiO_2/Na_2O$ mol ratio of the silicate were varied in the manner as shown in Examples 11–13. The results were substantially the same except with regard to those variables and results noted in Examples 11–13 in FIGS. 1 and 2.

EXAMPLES 26

The general procedures of Examples 1–25 were repeated except that potassium silicate was substituted for the sodium silicate. The results were substantially the same as in Examples 1–25.

EXAMPLE 27

In this experiment the determination and variables associated with the first occurance of the opalescence point as well as the importance of the "aging" at this point, were investigated The study revealed that a critical step in producing an acceptable aged silica is the determination of the opalescence point. For a given batch, the appearance of the opalescence point depends on the following:
Silicate concentration
Silicate mol ratio
Sulfuric acid concentration
Sulfuric acid rate The development work on aged silica was done by adding 11.4% sulfuric acid at the rate of 450 cc/min to 10 gallons of 2.5 mol ratio silicate of 13.3% concentration. The opalescence point appeared at 21 minutes and 15 seconds of acid addition. When the same batch was prepared with silicate of mol ratio 2.68, the opalescence point appeared at 19 minutes and 30 seconds. The processing advantages of the invention were found to be directly related to the determination of the opalescence point. If the reaction medium is aged by stopping acid about 30 seconds after the appearance of opalescence point, then about 50% of the process advantages are lost. By aging the reaction medium 60 seconds after the opalescence point, 100% of the processing advantages are lost and the product has properties similar to those produced by prior known processes. If the reaction medium is aged after stopping acid about 30 seconds before the opalescence point then an unacceptable product that is slow filtering and which exhibits significant changes in properties is obtained. Thus, an acceptable product can be produced only by stopping the acid addition and aging the reaction medium as soon as the opalescence point appears.

In this regard a Bailey, high range bolometer, was hooked up to the silica reactor to detect the opalescence point. It was observed that such a sensing device can be used effectively in detecting the opalescence point. It is important that the bolometer chamber be free of air bubbles; otherwise, a false opalescence point will be registered.

The following table (2) is a summary of the results of this study.

TABLE 2

| % WCM | SA($m^2/g$) | Oil Absorption (cc oil/100g) | M.R. Silicate | Final pH | Remarks* |
|---|---|---|---|---|---|
| 55 | 38 | 81 | 2.68 | 5.9 | 1 |
| 58 | 110 | 76 | 2.68 | 5.5 | 2 |
| 59 | 95 | 85 | 2.68 | 5.5 | 3 |
| 63 | 75 | 90 | 2.68 | 5.4 | 4 |

*1 = Aging done by stopping acid at opalescence
2 = Aging done by stopping acid at 60 seconds before opalescence point
3 = Aging done by stopping acid 30 seconds after opalescence point
4 = Aging done by stopping acid 60 seconds after opalescence point From the above it will be seen that the process of the instant invention results in a new product having a unique combination of physical and chemical properties. These include, e.g., low absorption, i.e., on the order of less than 125 cc/100 gm, wet cake moisture contents of less than 70%, surface areas of less than 100 $m^2/g$ when the adduct material is not added and in the range of from about 100-300 when the latter is employed; pack densities of greater than 12 lbs/ft$^3$ and valley abrasions of greater than 5 (mg. wire loss). Improved and very important processing advantages are also obtained. While particular embodiments have been disclosed for illustrative purposes the invention is not intended to be limited thereto. For example, in the case of silica production for a special utility the precipitating pH and the final slurry pH may be tailored accordingly. Also, and as should be readily appreciated by those skilled in the art, no special equipment is required in the method herein described. In this regard, however, the reactor should be equipped with heating means, e.g., a steam jacket, in order to maintain the desired reaction temperature and should have adequate agitating means to produce a strong backflow on the body of the liquid and thus avoid zones of high concentration of the incoming reactants. It is desirable to bring the reactants together so as to produce an instantaneous reaction of all material being fed to the fullest extent reasonably possible, as such promotes uniformity of the resulting products. Storage vessels (for the reactants) connected to the reaction vessel thru lines fitted with flow control means may also be provided. The reaction vessel may be equipped with an outlet line leading to a filter which may be of conventional design. As noted above, the filtered mass is washed and dried. Such steps may also be conducted in conventional equipment it being understood, of course, that same do not form a part of the present invention.

If the silicas of the invention are used in toothpaste compositions, the dentifrice (if in the form of a paste) may contain humectant materials and binders to give the dentifrice a smooth texture and good flowability. Glycerine sorbitol, corn syrup glucose and the like may be used as carriers. Examples of binders include gum tragacanth, sodium carboxy-methylcellulose and the like. The above materials as well as the specific formulation of the toothpaste are well known in the art and are disclosed for example in U.S. Pat. Nos. 2,994,642 and 3,538,230 and numerous publications.

What is claimed is:

1. A toothpaste comprising a binder effective to prevent separation of the solid and liquid phases, a particulate solid polishing agent and an aqueous liquid phase containing a humectant, characterized in that the polishing agent consists essentially of an amorphous precipitated silicic acid having a wet cake moisture content of less than 70%, an oil absorption of less than about 125 ccs/100 grams, a surface area of less than 300 $m^2/g$, a pack density of greater than about 12 lb./cu.ft., and a valley abrasion of greater than about 5 mg. wire loss, said precipitated silicic acid being non-opalescent silica aggregates grown to a larger controlled particle size and being present in an amount of from about 15 to about 50 percent by weight of the toothpaste and effective to function to remove stains, food, debris and plaque from the human tooth surface by providing ideal cleaning action at acceptable abrasion levels without thickening said toothpaste, said controlled larger particle size of said silica aggregates being thereby free of precipitated silicas which have substantially no cleaning ability on human teeth, have initially small particle sizes, and are free of the ease of breakdown into small particle sizes thus resulting in full cleaning ability.

2. A visually clear toothpaste comprising a binder effective to prevent separation of the solid and liquid phases, a particulate solid polishing agent and an aqueous liquid phase containing a humectant and having substantially the same refractive index as the polishing agent, characterized in that the polishing agent consists essentially of an amorphous precipitated silicic acid having a wet cake moisture content of less than 70%, an oil absorption of less than about 125 cc/100 grams, a surface area of 100 to 300 $m^2/g$, a pack density of greater than about 12 lb./cu.ft., and a valley abrasion of greater than about 5 mg. wire loss, and containing an adduct material selected from the group consisting of water soluble salts of aluminum, magnesium, calcium and zinc, said precipitated silicic acid being non-opalescent silica aggregates grown to a larger controlled particle size and being present in an amount of from about 15 to about 50 percent by weight of the toothpaste and effective to function to remove stains, food, debris and plaque from the human tooth surface by providing ideal cleaning action at acceptable abrasion levels without imparting undesirable opacity to the toothpaste or thickening said toothpaste, said controlled larger particle size of said silica aggregates being thereby free of precipitated silicas which have substantially no cleaning ability on human teeth, have initially small particle sizes, and are free of the ease of breakdown into small particle sizes thus resulting in full cleaning ability.

* * * * *

UNITED STATES PATENT AND TRADEMARK OFFICE
CERTIFICATE OF CORRECTION

PATENT NO. : 4,122,160
DATED : October 24, 1978
INVENTOR(S) : Satish K. Wason

It is certified that error appears in the above-identified patent and that said Letters Patent are hereby corrected as shown below:

Column 1, line 45, following "However," the word "the" should be -- and --.

Column 3, line 4, "preferrably" should be -- preferably --.
line 29, "have" should be -- has --.

Column 4, line 21, "preferrably" should be -- preferably --.
line 64, "partent" should be -- parent --.
line 66, "preferrably" should be -- preferably --.

Column 5, line 66, "(SiC$_2$" should be -- (SiO$_2$ --.

Column 6, line 50, "10.0" should be -- 10.1 --.

Column 9, lines 29 and 30, the following sentence should have been omitted: "The results are shown in FIGS. 1 and 2."

Column 11, line 38, the following phrase should have been omitted: "in FIGS. 1 and 2".
line 48, "occurance" should be -- occurrence --.
line 50, after "investigated" a period -- . -- should be inserted.

Column 13, line 19, following "syrup" a comma -- , -- should be inserted.

Signed and Sealed this

Twenty-seventh Day of March 1979

[SEAL]

Attest:

RUTH C. MASON
Attesting Officer

DONALD W. BANNER
Commissioner of Patents and Trademarks